United States Patent
Llewellyn

(12) 
(10) Patent No.: US 6,841,573 B2
(45) Date of Patent: Jan. 11, 2005

(54) USE OF ARACHIDONIC ACID AS A METHOD OF INCREASING SKELETAL MUSCLE MASS

(75) Inventor: William Charles Llewellyn, Sound Beach, NY (US)

(73) Assignee: Molecular Nutrition, Jupiter, FL (US)

( * ) Notice: Subject to any disclaimer, the term of this patent is extended or adjusted under 35 U.S.C. 154(b) by 149 days.

(21) Appl. No.: 10/306,265

(22) Filed: Nov. 27, 2002

(65) Prior Publication Data

US 2004/0102519 A1 May 27, 2004

(51) Int. Cl.$^7$ .................. A61K 31/202; A61K 31/20; A61K 31/22; A61K 31/19
(52) U.S. Cl. .............. 514/560; 514/557; 514/549; 514/558
(58) Field of Search ................. 514/560, 557, 514/549, 558

(56) References Cited

PUBLICATIONS

"Super Sterol Anabolic Complex", Product Information Brochure, www.amc–vitamins, 2001.*
"I'm confused, who would actually take this! (np)", stjames, www.dr–bob.org, Sep. 10, 2001.*
"Sterol Complex", Product Information Brochure, www.af-slabs.com, 2001.*
"Arachidonic Acid, Prostaglandin E2 and F2alpha Influences Rates of Protein Turnover in Skeletal and Cardiac Muscle", Rodemann et al., The Journal of Biological Chemistry, vol. 257, No. 4, 1982, pp. 1632–1638.*

* cited by examiner

*Primary Examiner*—Vickie Kim
*Assistant Examiner*—Brian S Kwon
(74) *Attorney, Agent, or Firm*—Holland & Knight LLP; Todd Hofmeister; Todd Parkhurst

(57) ABSTRACT

This invention discloses a method of orally administering arachidonic acid for the purpose of increasing the serum level of the prostaglandin PGF2alpha and subsequently the level of retained skeletal muscle mass.

1 Claim, No Drawings

USE OF ARACHIDONIC ACID AS A METHOD OF INCREASING SKELETAL MUSCLE MASS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Maintaining a healthy level of muscle mass can play an important role in sustaining overall good health, with benefits such as increased basal metabolic rate, better disposal of dietary fats and maintenance of lower body fat levels, increased immune system health, and an increase in one's overall vitality and sense of well-being compared to maintaining lower than ideal levels of lean body mass. A number of pathological conditions exist that make it difficult to maintain a normal healthy level of muscle mass, including HIV (human immunodeficiency virus), andropause or hypogonadism (subnormal androgen levels), infection, trauma, burns, and spinal cord injury. Some individuals also fail to gain or to maintain normal lean body mass without definite pathophysiologic reasons. Many treatments are offered that would help an individual in need of such treatment promote the buildup of muscle tissue.

Skeletal muscle mass is increased or maintained in the body through a number of separate and distinct mechanisms. Such mechanisms play a role in the regulation of either skeletal muscle protein synthesis or breakdown, and collectively control the total amount of accrued protein present in the muscle cell. The actions of androgens are among the most visibly tied to the regulation of skeletal muscle mass, as these hormones are collectively responsible for the development and maintenance of male sexual characteristics including external virilization, sexual maturity at puberty, spermatogenesis, sexual behavior/libido and erectile functioning and the support of bone and muscle tissue growth. It is well documented in the prior art that raising the level of androgenic hormones in the body can increase skeletal muscle mass. A number of methods have similarly been developed to increase the level of androgenic hormones in the body, which ultimately can be used to offer the benefits of increased skeletal muscle mass in humans.

In searching for ways to increase androgen levels in the body, the use of androgen precursor hormones have been suggested. U.S. Pat. No. 5,578,588 to Mattem et al. relates a method of using a precursor hormone, namely androstenedione, as a means of increasing testosterone levels. Although the in-vivo conversion of endogenous androstenedione to testosterone had been documented and cited in this patent, the use of this compound as an external supplement for producing a stable and effective increase in serum testosterone had never been investigated before, and therefore represents a novel invention. The pharmacokinetics of administering such a precursor is such that hormone concentrations of active hormone (testosterone) peak within 90 minutes, and subsequently decline over a period of three to four hours. This more closely resembles the natural pulsating pattern in which the body releases testosterone, and avoids the prolonged peaks and troughs noted with use of esterified injectable hormone preparations.

Several other methods of using different androgen precursor hormones have also been disclosed, including U.S. Pat. No. 5,880,117 to Patrick Arnold, which relates a method of using 4-androstenediol as a means of increasing testosterone levels in humans. This in-vivo conversion of 4-androstenediol to testosterone, again, was well documented in the prior art and this patent, however the use of this compound as an effective oral medicament for raising testosterone levels was never investigated prior, and therefore represents another novel invention. U.S. Pat. No. 6,391,868 to Arnold similarly relates a method of using 5-alpha-androst-1-en-3-one for increasing levels of the anabolic/androgenic steroid 17-beta-hydroxy-5-alpha-androst-1-en-3-one in humans. Again the in-vivo bioconversion was known, however a formal investigation of its oral use to increase serum androgen levels had never been disclosed. U.S. Pat. No. 6,262,436 to Llewellyn further discloses the method of using 5-alpha-androstanedione or 5-alpha-androstanediol to increase levels of dihydrotestosterone in humans, a hormone which also offers the benefit of regulating protein synthesis and increasing skeletal muscle mass.

The use of androgenic hormones in general, however, is often thought to entail some risk, as increasing the level of such hormones may also be relevant to the development of undesirable side effects such as gynecomastia, water retention (edema), unfavorable alterations in cholesterol levels (increased heart disease risk) and increased blood pressure to name just a few. If an individual is seeking solely to increase skeletal muscle mass, and is not in need of androgen replacement, then the methods regarding the use of androgen precursors may be less than ideal. It therefore became to focus of this inventor to find another distinct mechanism in the body that plays an important role in the regulation of protein synthesis, and can be affected externally by the similar use of a precursor compound to an active constituent in said mechanism to enhance the buildup of skeletal muscle tissue.

This invention relates a method of administering arachidonic acid for the purpose of increasing the level of the prostaglandin PGF2alpha and subsequently skeletal muscle mass. PGF2alpha is not an androgenic steroid, but an endogenous prostaglandin. It is referred to commonly as an inflammatory hormone, and is related to several biological functions including immunity, response to allergens, intestinal mobility and blood flow in various regions of the body. PGF2alpha is also closely tied to skeletal muscle protein synthesis in the body (Biochem J 1983 Sep. 15;214(3):1011–4), and represents an important new target for the external modulation of skeletal muscle mass distinct from the mechanisms involving male sex steroids. This method of using arachidonic acid for increasing PGF2alpha and skeletal muscle mass is an ideal solution for an individual in need of such treatment, because PGF2alpha is non-steroidal, and can increase protein synthesis and muscle mass without the potential undesirable side effects associated with altering sex steroid levels with androgen precursor hormones.

BRIEF SUMMARY OF THE INVENTION

Prior art relates several novel methods of using precursors to hormones that regulate protein synthesis for the purpose of increasing the levels of said hormones, which ultimately can increase skeletal muscle mass. Although the suggested practice of using precursors to physiologically active hormones seems quite sound, the target hormones in the cited art, namely androgenic steroids, may be less than ideal in many cases, particularly in those where increases in skeletal muscle mass are desired but the potential side effects of androgens contraindicates their use. The problem of the present invention is therefore to provide a precursor to a target hormone that can also be used to increase skeletal muscle mass when administered, but is completely non-steroidal. According to the invention this problem is solved by the oral use of arachidonic acid, a direct precursor to the prostaglandin PGF2alpha. This method is ideal because it is natural, non-toxic, quickly metabolized to active form after oral administration, and can increase skeletal muscle mass without the potential side effects of androgenic precursors.

BRIEF DESCRIPTION OF THE SEVERAL VIEWS OF THE DRAWING

Not Applicable

DETAILED DESCRIPTION OF THE INVENTION

Arachidonic acid is a naturally occurring polyunsaturated fat, belonging to the Omega-6 family of fatty acids. It is considered an essential fatty acid (EFA), because it is an essential nutrient that your body can't produce itself. The only way you can get arachidonic acid is through the food you eat. It is obtained in small amounts in the average human diet, coming from various plant and animal sources including milk. Arachidonic acid has furthermore been identified as a vital precursor to numerous hormones in the body including prostaglandins, prostacyclin (PGI12), leukotrienes, and thromboxanes.

Studies by have fundamentally proven the in-vitro conversion of arachidonic acid to the prostaglandin PGF2alpha. Experiments by Berlin et al. (Acta Physiol Scand 1979 August;106(4):441–5) used 14C-labeled arachidonic acid to chart the metabolism of this essential fatty acid into various prostaglandins in human skeletal muscle and kidney homogenates. Those prostaglandins produced during this incubation include PGD2, PGE2, PGF2 alpha and 6-keto-PGF1 alpha. Further studies with labeled arachidonic acid have fundamentally proven the in-vivo conversion of this fatty acid into PGF2alpha (Acta Physiol Scand 1979 July;106(3):307–12). In this investigation the labeled metabolites of arachidonic acid were measured in serum extracted from the forearm and kidney of human volunteers after direct infusion into the brachial or renal artery. PGD2, PGE2, PGF2 alpha, 6-keto-PGF1 alpha and 13,14-dihydro-15-keto-PGE2 (Me) were all found in this experiment.

The prostaglandin PGF2alpha has also been proven to play a vital role in skeletal muscle protein synthesis. In fact, it is one of the prostaglandins most closely tied to protein synthesis, and therefore the primary focus of this invention. Studies conducted by Smith et al. (Biochem J 1983 July 15;214(1):153–61) have fundamentally proven the importance of PGF2alpha in stimulating protein synthesis in-vitro, by testing the effects of various arachidonic acid metabolites when incubated with intact rabbit muscle that was intermittently placed under stretch stimulus. In this study two prostaglandins, F2 alpha and A1, increased rates of protein synthesis in unstimulated muscles, but prostaglandins E2 and D2 and the leukotrienes C4 and D4 failed to do so. Further studies with the cox-1 enzyme inhibitors ibuprofen and acetaminophen, which exhibit their anti-inflammatory actions by inhibiting the synthesis of prostaglandins, suggest that these drugs can profoundly diminish the anabolic response of muscle to resistance exercise by inhibiting the normal post-exercise increase in levels of PGF2alpha (Clin Endocrinol Metab 2001 October;86(10):5067–7). A search of the prior art does not reveal any investigations into what effect additional arachidonic acid in the diet would have on total protein synthesis or skeletal muscle mass.

Prior art also does not disclose any investigations regarding the effect oral arachidonic acid would have on the serum level of PGF2alpha. Human tests carried out by Kelley et al. (Lipids 1998 February:33(2):125–30), however, did look at the effect of oral arachidonic acid on in-vitro immune response as measured by the secretion of different prostaglandins and immune system factors. In this study, the in-vitro secretion of LTB4 and PGE2, as demonstrated by influenza antibody titers determined on drawn blood, did seem to measurably increase after oral administration of 200 mg and 1.5 g of supplemented arachidonic acid per day. This suggested to this inventor that a similar increase might be noted in-vivo with other prostaglandins not measured in this experiment including PGF2alpha.

After learning of the in-vitro and in-vivo conversion of arachidonic acid to PGF2alpha, plus the role PGF2alpha plays in the regulation of skeletal muscle protein synthesis, it became the focus of this invention that skeletal muscle mass can be increased by the oral administration of arachidonic acid. In an effort to prove this theory a clinical study was therefore undertaken by the inventor. Specifically, it was the intention of this inventor to prove that arachidonic acid would act as an effective in-vivo peroral PGF2alpha precursor in man capable of raising and sustaining elevated PGF2alpha levels, and that the resultant increases in levels of PGF2alpha would result in increases in the level of skeletal muscle mass.

An effective oral daily dosage of arachidonic acid is between 100 mg to 5,500 mg. It is ideally provided as a soft gelatin capsule or oral liquid, due to the fact that arachidonic acid is in the form of free flowing oil at room temperature. Due to the rapidity in which the discussed compound is metabolized in the body, the total daily dosage can be further subdivided for a more sustained blood hormone concentration, with 2–3 applications per day being most preferred.

What is claimed is:

1. A method for increasing muscle mass, which method comprises administering orally to a human in need of such treatment an amount of arachidonic acid between about 100 mg and 5,500 mg which is effective in raising the level of the endogenous prostaglandin PGF2 alpha.

* * * * *